United States Patent
Yamamoto (10) Patent No.: US 9,901,730 B2
(45) Date of Patent: Feb. 27, 2018

(54) STOPCOCK FLOW PATH SWITCHING DEVICE

(75) Inventor: Tetsuya Yamamoto, Osaka (JP)

(73) Assignee: SUGAN CO., LTD., Osaka (JP)

( * ) Notice: Subject to any disclaimer, the term of this patent is extended or adjusted under 35 U.S.C. 154(b) by 455 days.

(21) Appl. No.: 14/418,942

(22) PCT Filed: Jul. 31, 2012

(86) PCT No.: PCT/JP2012/069435
§ 371 (c)(1),
(2), (4) Date: Jan. 31, 2015

(87) PCT Pub. No.: WO2014/020692
PCT Pub. Date: Feb. 6, 2014

(65) Prior Publication Data
US 2015/0202425 A1    Jul. 23, 2015

(51) Int. Cl.
*A61M 39/22* (2006.01)
*A61B 5/0215* (2006.01)
(Continued)

(52) U.S. Cl.
CPC ......... *A61M 39/223* (2013.01); *A61B 5/0215* (2013.01); *A61B 5/02141* (2013.01); *A61M 5/007* (2013.01); *A61M 2039/229* (2013.01)

(58) Field of Classification Search
CPC ............. A61B 5/02141; A61B 5/0215; A61M 2039/229; A61M 39/223; A61M 5/007;
(Continued)

(56) References Cited

U.S. PATENT DOCUMENTS 5,968,015 A  10/1999  Yamamoto
6,004,285 A  12/1999  Sugahara
(Continued)

FOREIGN PATENT DOCUMENTS

CN  1299454 A  6/2001
CN  1582175 A  2/2005
(Continued)

OTHER PUBLICATIONS

Chinese Office Action dated Sep. 29, 2016 issued in Chinese Patent Application No. 201280074978.1 (with English translation).
(Continued)

*Primary Examiner* — Bhisma Mehta
*Assistant Examiner* — Brandy S Lee
(74) *Attorney, Agent, or Firm* — McDermott Will & Emery LLP (57) ABSTRACT

This stopcock flow path switching device includes: a three-way stopcock having a flow path switching cock and provided to, by switching of the flow path switching cock, allow flow path switching between a state in which a contrast agent introducing flow path is formed by coupling a flow path on the patient side to a flow path on the injector head side and a state in which a blood pressure measuring flow path is formed by coupling the flow path on the patient side to a flow path on the blood pressure transducer side; and a clamp mechanism for closing the flow path of the three-way stopcock communicating with the injector head side, in the state in which the blood pressure measuring flow path is formed.

2 Claims, 11 Drawing Sheets

(51) Int. Cl.
*A61M 5/00* (2006.01)
*A61B 5/021* (2006.01)

(58) Field of Classification Search
CPC .... A61M 39/28; A61M 31/005; A61M 39/22; A61M 39/285
See application file for complete search history.

(56) References Cited

U.S. PATENT DOCUMENTS

| | | | |
|---|---|---|---|
| 6,530,907 B1 | 3/2003 | Sugahara et al. | |
| 2005/0004447 A1* | 1/2005 | Yamamoto | A61M 5/16827 600/420 |
| 2005/0245873 A1 | 11/2005 | Nemoto | |
| 2010/0191106 A1* | 7/2010 | Koyama | A61M 39/223 600/431 |

FOREIGN PATENT DOCUMENTS

| | | |
|---|---|---|
| CN | 1671440 A | 9/2005 |
| CN | 101678198 A | 3/2010 |
| JP | 07-100212 A | 4/1995 |
| JP | H09-108360 A | 4/1997 |
| JP | 10-165396 A | 6/1998 |
| JP | 10-244002 A | 9/1998 |
| JP | 2000-325485 A | 11/2000 |
| JP | 2003-199823 A | 7/2003 |
| JP | 2004-065737 A | 3/2004 |
| WO | 2011/118410 A1 | 9/2011 |

OTHER PUBLICATIONS

International Search Report issued in International Application No. PCT/JP2012/069435 dated Sep. 11, 2012, with English Translation.

* cited by examiner

PATIENT

BLOOD PRESSURE

FIG.16

STOPCOCK FLOW PATH SWITCHING DEVICE

RELATED APPLICATIONS

This application is a national phase of International Application No. PCT/JP2012/069435, filed on Jul. 31, 2012, the disclosure of which Application is incorporated by reference herein.

TECHNICAL FIELD

The present invention relates to a stopcock flow path switching device coupled to an injector head for introducing a contrast agent or other liquid medicines into a patient.

BACKGROUND ART

In a cardiac catheter test, a contrast agent is introduced to a patient using an injector head, and the test is done while imaging the affected part. For example, utilizing a coronary angiography of providing images of cardiac blood vessels, an operation of blood vessel is performed for widening a narrowed lesion by catheter method. Utilizing left ventricular angiogram imaging the left ventricle of the heart, behavior of cardiac muscle around the left ventricle is tested, by monitoring systole and diastole states of the heart.

Examples of such an injector head are disclosed, for example, in Japanese Patent Laying-Open Nos. 10-165396 (PTD 1) and 10-244002 (PTD 2).

CITATION LIST

Patent Document

PTD 1: Japanese Patent Laying-Open No. 10-165396
PTD 2: Japanese Patent Laying-Open No. 10-244002

SUMMARY OF INVENTION

Technical Problem

When the test is done using the injector head, the blood pressure of the patient is measured as appropriate. A blood pressure transducer is used to measure the blood pressure of the patient. A switching mechanism for switching between a flow path for coupling the patient to the injector head (hereinafter, contrast agent introducing flow path) and a flow path for coupling the patient to the transducer (hereinafter, blood pressure measuring flow path) is provided somewhere in a flow path for introducing the contrast agent from the injector head into the patient.

When the test is done using the injector head, more accurate measurement of the patient's blood pressure is important. As for the aforementioned switching mechanism as well, it is important to use a switching mechanism that does not affect blood pressure measurement in switching between the contrast agent introducing flow path and the blood pressure measuring flow path.

Therefore, the present invention has been made to solve the aforementioned problem and an object thereof is to provide a stopcock flow path switching device including a configuration that allows more accurate measurement of the patient's blood pressure in switching between a contrast agent introducing flow path and a blood pressure measuring flow path.

Solution to Problem

A stopcock flow path switching device according to the present invention is a stopcock flow path switching device used to switch between a contrast agent introducing flow path for introducing a contrast agent into a patient by using an injector head and a blood pressure measuring flow path for measuring a blood pressure of the patient by using a blood pressure transducer, the stopcock flow path switching device including: a three-way stopcock having a flow path switching cock and provided to, by switching of the flow path switching cock, allow flow path switching between a state in which the contrast agent introducing flow path is formed by coupling a flow path on the patient side to a flow path on the injector head side and a state in which the blood pressure measuring flow path is formed by coupling the flow path on the patient side to a flow path on the blood pressure transducer side; and a clamp mechanism for closing the flow path of the three-way stopcock communicating with the injector head side, in the state in which the blood pressure measuring flow path is formed.

According to another aspect, the stopcock flow path switching device further includes a switching-linked mechanism for controlling the clamp mechanism in accordance with a switching position of the flow path switching cock of the three-way stopcock, such that a first flow path coupled to the three-way stopcock and communicating with the injector head side is opened in the state in which the contrast agent introducing flow path is formed, and the first flow path coupled to the three-way stopcock and communicating with the injector head side is blocked in the state in which the blood pressure measuring flow path is formed.

According to another aspect, the clamp mechanism has a fixed valve element and a movable valve element arranged on an outer side of the first flow path to face each other to sandwich the first flow path, and the switching-linked mechanism moves the movable valve element to a position farthest from the fixed valve element and opens the first flow path in the state in which the contrast agent introducing flow path is formed, and moves the movable valve element to a position closest to the fixed valve element, sandwich the first flow path between the movable valve element and the fixed valve element and blocks the first flow path in the state in which the blood pressure measuring flow path is formed.

According to another aspect, the switching-linked mechanism includes: an eccentric cam roller provided at the flow path switching cock and provided to have a rotation center identical to that of the flow path switching cock; a supporting part having a rotation center; a first link bar and a second link bar provided at the supporting part and extending from the supporting part in different directions; the movable valve element provided at a tip end of the first link bar; and a sliding roller provided at a tip end of the second link bar and constantly abutting a side surface of the eccentric cam roller.

In the state in which the contrast agent introducing flow path is formed, the sliding roller is located at a position closest to the rotation center of the eccentric cam roller and the movable valve element is located at the position farthest from the fixed valve element, and in the state in which the blood pressure measuring flow path is formed, the sliding roller is located at a position farthest from the rotation center of the eccentric cam roller and the movable valve element is located at the position closest to the fixed valve element.

According to another aspect, in the flow path on the blood pressure transducer side, a stopcock is provided for opening and closing the flow path on an opposite side of the three-way stopcock with the blood pressure transducer interposed therebetween.

Advantageous Effects of Invention

According to the stopcock flow path switching device of the present invention, there can be provided a stopcock flow path switching device including a configuration that allows more accurate measurement of the patient's blood pressure in switching between a contrast agent introducing flow path and a blood pressure measuring flow path.

DESCRIPTION OF EMBODIMENTS

Before describing a stopcock flow path switching device in accordance with the present embodiment, an injector head will be first described as the related art. In the related art and the embodiments described below, the same or corresponding components will be denoted by the same reference characters, and description thereof may not be repeated. Any numbers and amounts mentioned are not limiting the scope of the invention, unless specifically described to the contrary.

In the figures, for easier understanding of the contrast agent in the syringe, piston position and plunger position, the syringe is shown in cross-sections. The priming orientation refers to a state for performing a preliminary work (such as filling the syringe with the contrast agent) before injecting the contrast agent, and the contrast agent injectable orientation refers to the orientation ready to start injection of the contrast agent and the orientation during injection of the contrast agent.

(Injector Head 1)

Figure 1:
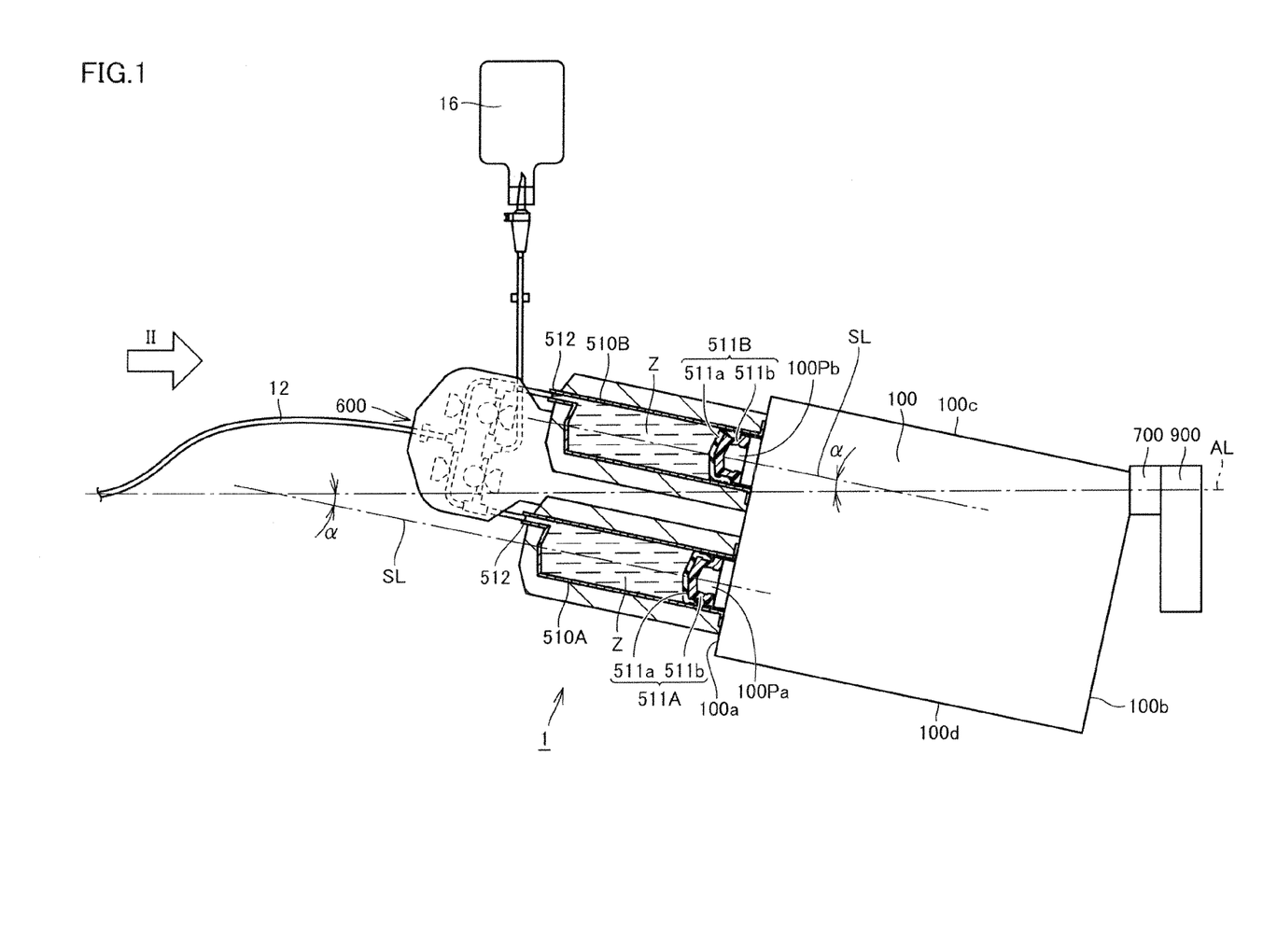
FIG. 1 is a side view showing an injector head (in priming orientation) in accordance with the related art.
Figure 2:
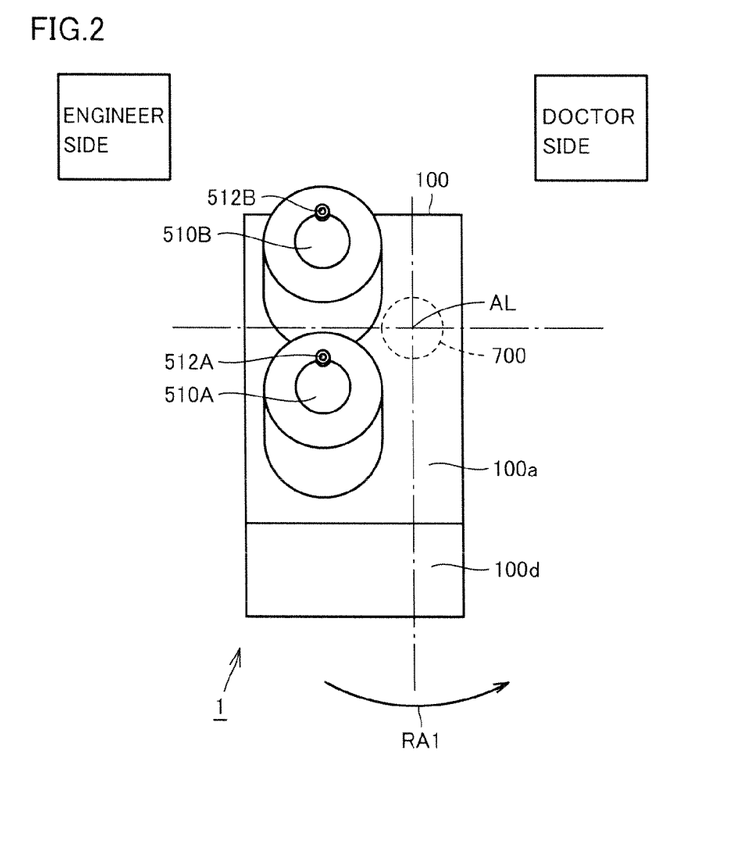
FIG. 2 is a view from a direction of an arrow II of FIG. 1.
Figure 3:
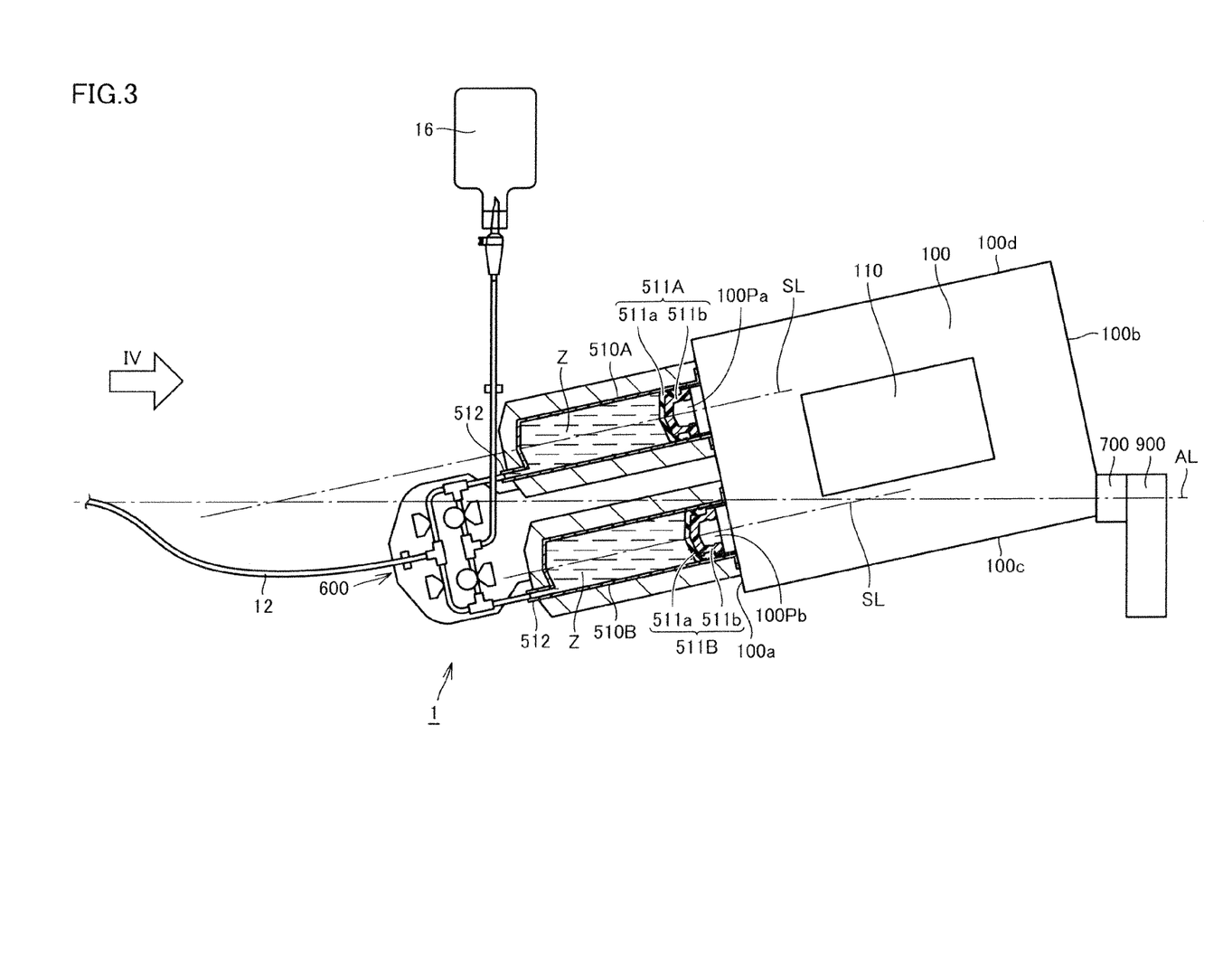
FIG. 3 is a side view showing the injector head (in contrast agent injectable orientation) in accordance with the related art.
Figure 4:
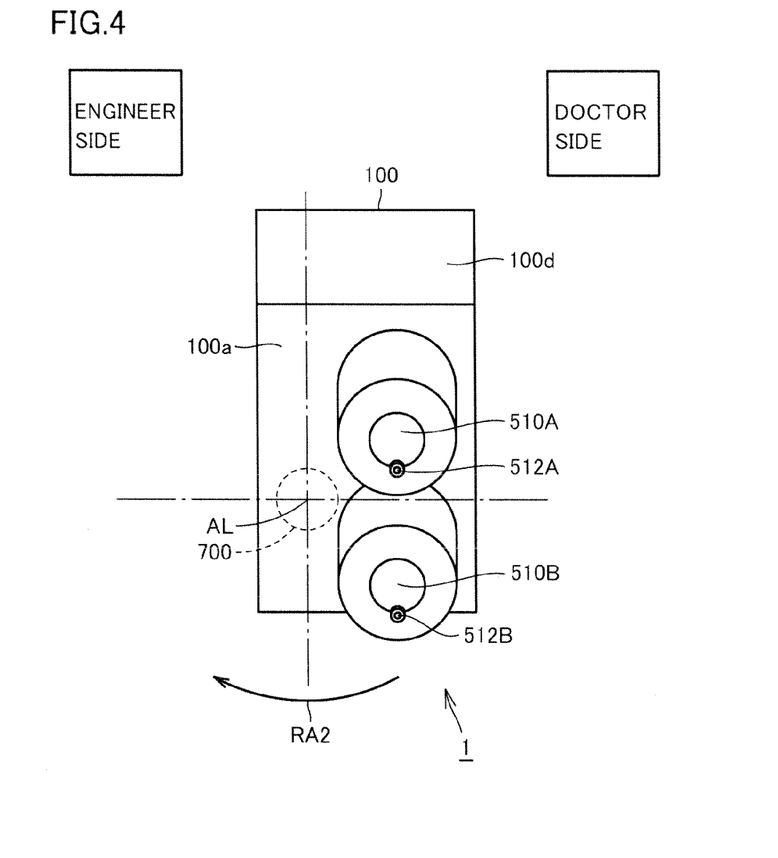
FIG. 4 is a view from a direction of an arrow IV of FIG. 3.
Figure 5:
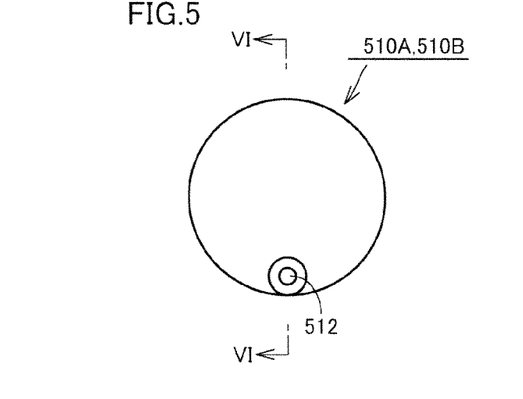
FIG. 5 is a side view from a direction of an arrow V of FIG. 6, of a syringe attached to the injector head in accordance with the related art.
Figure 6:
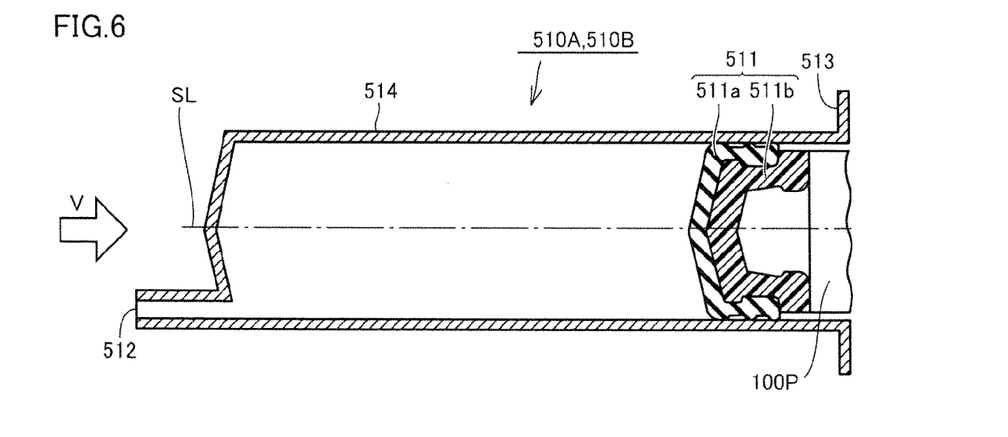
FIG. 6 is a cross-sectional view taken along the line VI-VI of FIG. 5, of the syringe attached to the injector head in accordance with the related art.

Referring to FIGS. 1 to 6, an injector head 1 will be described. FIG. 1 is a side view showing injector head 1 (in priming orientation). FIG. 2 is a view from a direction of an arrow II of FIG. 1, FIG. 3 is a side view showing injector head 1 (in contrast agent injectable orientation), and FIG. 4 is a view from a direction of an arrow IV of FIG. 3. FIG. 5 is a side view from a direction of an arrow V of FIG. 6, of a syringe attached to the injector head, and FIG. 6 is a cross-sectional view taken along the line VI-VI of FIG. 5, of the syringe attached to the injector head.

Injector head 1 has a rotation mechanism and includes: a support post 900 as a supporting part; a rotating part 700 fixed on support post 900 to have its rotation axis AL extending substantially horizontally; an injector head body 100 fixed to rotating part 700 to be rotatable about rotation axis AL as the center of rotation; and first and second syringes 510A and 510B detachably attached to injector head body 100. A roller bearing or the like is used for rotating part 700.

To a through hole 512 formed at the front end portion of each of first and second syringes 510A and 510B, a liquid medicine flow path switching device 600 is coupled. Details of liquid medicine flow path switching device 600 will be described later. On a side surface of injector head body 100, an operation monitor 110 implemented by a touch-panel is provided (see FIG. 3).

As first and second syringes 510A and 510B, a syringe having such a shape as shown in FIGS. 5 and 6 is used. The syringe has a cylindrical part 514 having the front end side closed and the back end side opened to receive a piston 511 to be fit in liquid-tight manner, through hole 512 provided on the front end side, and a flange 513 provided on the back end side.

Piston 511 includes a piston rubber 511a and a piston core 511b covered by piston rubber 511a. To piston core 511b, a plunger 100P provided inside injector head body 100 is coupled. Cylindrical part 514 is fixed on injector head body 100.

As plunger 100P moves forward and backward, piston 511 also moves forward/backward in cylindrical part 514. Piston rubber 511a moves while maintaining liquid-tightness with respect to the inner circumferential surface of cylindrical part 514.

Syringe 510 in accordance with the present embodiment has through hole 512 at a position eccentric from a central axis line SL of syringe 510. The central axis line of syringe 510 means a phantom line extending from the front end side to the back end side and passing through the central axis of syringe 510.

Again referring to FIGS. 1 to 4, in a state where first and second syringes 510A and 510B are attached to injector head body 100, when viewed from a direction perpendicular to and parallel to rotation axis AL (in a direction perpendicular to the drawing sheet), central axis lines SL of first and second syringes 510A and 510B are inclined from rotation axis AL.

When viewed from the direction perpendicular to and parallel to rotation axis AL (in a direction perpendicular to the drawing sheet), the angle (α) at which central axis line SL and rotation axis AL intersect is about 5 to about 30 degrees, preferably about 7 to about 25 degrees, and more preferably about 10 to about 15 degrees.

Specifically, referring to FIG. 1, injector head body 100 has a substantially rectangular parallelepiped shape, first and second syringes 510A and 510B are attached to a first surface 100a of injector head body 100, and rotating part 700 is fixed to an area at an upper corner (near a third surface 100c) of a second surface 100b opposite to first surface 100a. In the shown example, first and second syringes 510A and 510B are filled with a contrast agent Z.

In the priming orientation shown in FIGS. 1 and 2, third surface 100c positioned on the upper side between first and second surfaces 100a and 100b is inclined upward from the side of second surface 100b to the side of first surface 100a, and a fourth surface 100d positioned on the lower side between first and second surfaces 100a and 100b is also inclined upward from the side of second surface 100b to the side of first surface 100a.

Further, in the priming orientation, first and second syringes 510A and 510B are attached to injector head body 100 such that through hole 512 of each of first and second syringes 510A and 510B is positioned at the uppermost side.

As shown in FIGS. 3 and 4, in the contrast agent injectable orientation with injection head body 100 rotated (in the direction of an arrow RA1 of FIG. 2) about rotation axis AL as the center of rotation, fourth surface 100d positioned on the upper side between first and second surfaces 100a and 100b is inclined downward from the side of second surface 100b to the side of first surface 100a, and fourth surface 100d positioned on the lower side between first and second surfaces 100a and 100b is also inclined downward from the side of second surface 100b to the side of first surface 100a.

By rotating injector head body 100 about rotation axis AL as the center of rotation, this injector head 1 can selectively be set to a state (the state shown in FIGS. 1 and 2) in which first and second syringes 510A and 510B assume the priming orientation with through holes 512 of first and second syringes 510A and 510B positioned upper than injector head body 100, and a state (the state shown in FIGS. 3 and 4) in which first and second syringes 510A and 510B assume the contrast agent injectable orientation with through holes 512 of first and second syringes 510A and 510B positioned lower than injector head body 100.

In the priming orientation shown in FIGS. 1 and 2, when viewed from the direction perpendicular to and parallel to rotation axis AL, central axis line SL of first syringe 510A intersects rotation axis AL on the side of through hole 512 of first syringe 510A. In the contrast agent injectable orientation shown in FIGS. 3 and 4, first syringe 510A is attached to injector head body 100 such that, when viewed from the direction perpendicular to and parallel to rotation axis AL, central axis line SL of first syringe 510A intersects rotation axis AL on the side of injector head body 100 of first syringe 510A.

In the priming orientation shown in FIGS. 1 and 2, when viewed from the direction perpendicular to and parallel to rotation axis AL, central axis line SL of second syringe 510B intersects rotation axis AL on the side of injector head body 100 of second syringe 510B.

In the contrast agent injectable orientation shown in FIGS. 3 and 4, second syringe 510E is attached to injector head body 100 such that, when viewed from the direction perpendicular to and parallel to rotation axis AL, central axis line SL of second syringe 510B intersects rotation axis AL on the side of through hole 512 of second syringe 510B.

Consequently, even when injector head body 100 rotates between the "priming orientation" shown in FIGS. 1 and 2 and the "contrast agent injectable orientation" shown in FIGS. 3 and 4, a coupling tube 12 extending from liquid medicine flow path switching device 600 coupled to first and second syringes 510A and 510B moves only around rotation axis AL.

As a result, interference between coupling tube 12 coupled to this injector head 1 and other devices becomes less likely. Therefore, ample margin for the tube length becomes unnecessary. Further, the burden on the engineer paying attention to avoid contact between the tube and other devices can be alleviated.

Though double-syringe type injector head 1 having two syringes has been described above, the number of syringes is not limited to two, and the invention is also applicable to a single-syringe type injector head using either one of the syringes.

Though a syringe having through hole 512 eccentric to a central axis line CL is used as syringe 510, a syringe having through hole 512 provided on central axis line CL may be used.

(Contrast Agent Introducing Flow Path L1000)

Figure 7:
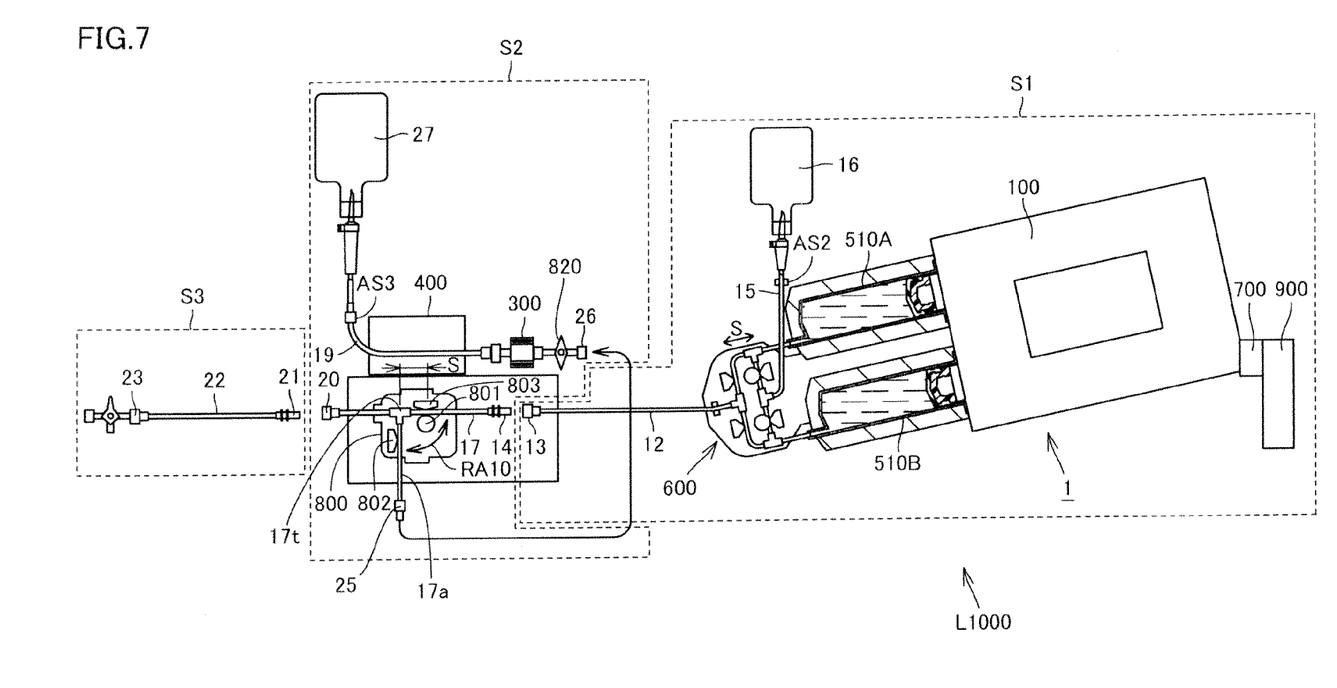
FIG. 7 is a view showing a contrast agent introducing flow path to a patient when a flow path switching device is used in the injector head in accordance with the related art.

Next, a contrast agent introducing flow path L1000 to the patient using injector head 1 having the structure above will be described with reference to FIG. 7. To first and second syringes 510A and 510B attached to injector head body 100, liquid medicine flow path switching device 600 is coupled. Details of this liquid medicine flow path switching device 600 will be described later.

Contrast agent introducing flow path L1000 can be divided to a multi-use section S1 used for a plurality of patients, and one-time use sections S2 and S3 used only for one patient.

Multi-use section S1 will be described. Multi-use section S1 is shown by an area including injector head 1 surrounded by dotted lines in FIG. 7. Multi-use section S1 has liquid medicine flow path switching device 600. To liquid medicine flow path switching device 600, a seventh tube 15 is coupled, and to this seventh tube 15, a contrast agent bag 16 is coupled. To liquid medicine flow path switching device 600, coupling tube 12 leading to the patient is coupled. At the tip end of coupling tube 12, a connector 13 is connected.

One-time use section S2 will be described. One-time use section S2 is shown by an area surrounded by dotted lines in FIG. 7. One-time use section S2 has a main tube 17 having a connector 14 connected to one end and a connector 20 connected to the other end. Connector 14 is connected to connector 13 of coupling tube 12.

By using a T-shaped tube 17t, a branch tube 17a is coupled to main tube 17. At the tip end of branch tube 17a, a connector 25 is connected. Opening/closing of main tube 17 and branch tube 17*a* is controlled by a contrast agent/blood pressure flow path switching device 800.

Contrast agent/blood pressure flow path switching device 800 has a change-over valve element 801 and fixed valve elements 802 and 803, and change-over valve element 801 is controlled to be movable in the direction of an arrow RA10 in the figure. By change-over valve element 801 and fixed valve element 803, opening/closing of main tube 17 is controlled, and by change-over valve element 801 and fixed valve element 802, opening/closing of branch tube 17*a* is controlled.

Connector 25 of branch tube 17*a* is coupled to a connector 26 provided on a normal saline tube 19. Normal saline tube 19 has the other end coupled to a saline bag 27. A stopcock 820, a blood pressure transducer 300, a roller pump 400, and a third air sensor AS3 are provided on normal saline tube 19.

One-time use section S3 will be described. One-time use section S3 is shown by an area on the patient side surrounded by dotted lines in the figure. One-time use section S3 has a tube 22 having a connector 21 connected to one end and a connector 23 connected to the other end. To connector 21, connector 20 of main tube 17 is coupled. To connector 23, a catheter inserted to a blood vessel of a patient is coupled.

When the contrast agent is to be introduced from injector head 1 to the patient, branch tube 17*a* is closed and main tube 17 is opened by change-over valve element 801 and fixed valve element 802.

Blood pressure of a patient is measured, with main tube 17 closed by change-over valve element 801 and fixed valve element 803 and branch tube 17*a* communicated with saline bag 27. For the measurement of blood pressure, electric signals from blood pressure transducer 300 are used.

As described above, the blood pressure of a patient is measured, with main tube 17 closed by change-over valve element 801 and fixed valve element 803, and branch tube 17*a* opened and communicated with saline bag 27.

At this time, the portion on the multi-use section S1 side when viewed from T-shaped tube 17*t* of main tube 17 is sandwiched between change-over valve element 801 and fixed valve element 803. Therefore, entry of the patient's blood to multi-use section S1 is prevented.

However, the area of main tube 17 sandwiched between fixed valve element 803 and change-over valve element 801 is located at a location distant toward the multi-use section S1 side when viewed from T-shaped tube 17*t* (a distance S in the figure). Therefore, it is conceivable that the electric signals from blood pressure transducer 300 become dull by an amount corresponding to this distance S. Consequently, the electric signals from blood pressure transducer 300 may need to be corrected.

(First Embodiment: Stopcock Flow Path Switching Device)

Figure 8:
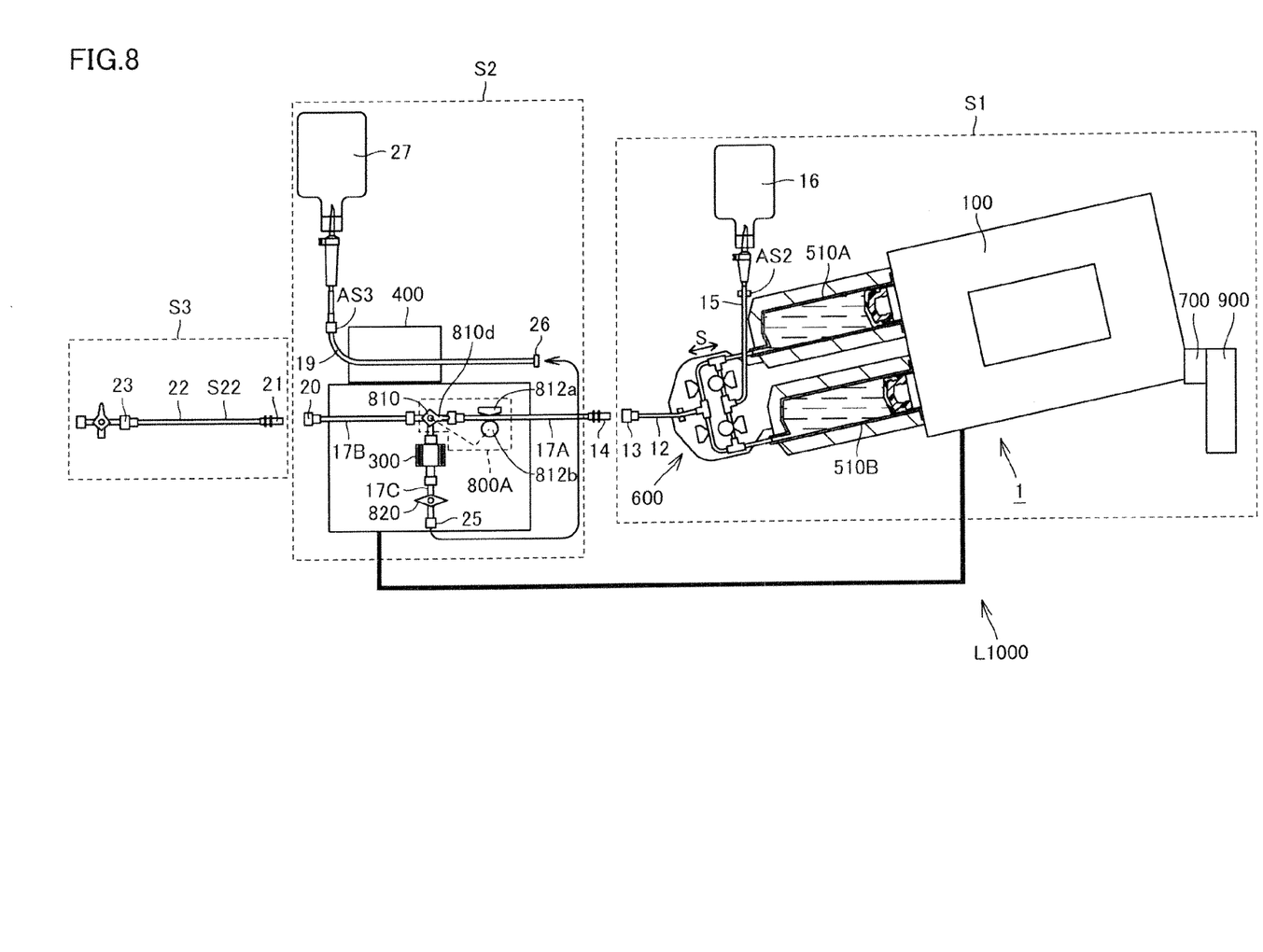
FIG. 8 is a view showing a contrast agent introducing flow path to the patient when a stopcock flow path switching device is coupled to the injector head in accordance with a first embodiment.

A stopcock flow path switching device 800A as a contrast agent/blood pressure flow path switching device in accordance with the present embodiment will be described with reference to FIG. 8. FIG. 8 is a view showing contrast agent introducing flow path L1000 to the patient when stopcock flow path switching device 800A in accordance with the present embodiment is coupled to injector head 1.

This stopcock flow path switching device 800A has a three-way stopcock 810, and one end of each of a first tube (first flow path) 17A, a second tube (second flow path) 17B and a third tube (third flow path) 17C is coupled to this three-way stopcock 810. First tube 17A is coupled to the injector head 1 side, second tube 17B is coupled to the patient side, and third tube 17C is coupled to the blood pressure transducer 300 side.

Connector 14 is provided at the other end of first tube 17A. Connector 14 of first tube 17A is connected to connector 13 of coupling tube 12 provided in multi-use section S1.

Connector 20 is provided at the other end of second tube 17B. Connector 20 of second tube 17B is connected to connector 21 of tube 22 provided in one-time use section S3.

Connector 25 is provided at the other end of third tube 17C. Connector 25 of third tube 17C is connected to connector 26 provided on normal saline tube 19. Blood pressure transducer 300 and stopcock 820 are provided in third tube 17C. As described with reference to FIG. 7, blood pressure transducer 300 and stopcock 820 may be provided on the normal saline tube 19 side.

Three-way stopcock 810 described above is provided to, by pivoting a flow path switching cock 810*d* with a drive motor, allow switching between a state in which the flow path contrast agent introducing flow path for coupling the patient to the injector head is formed by communicating first tube 17A with second tube 17B and closing third tube 17C, and a state in which the blood pressure measuring flow path for coupling the patient to the transducer is formed by communicating first tube 17A with third tube 17C and closing second tube 17B.

Stopcock flow path switching device 800A has a clamp mechanism 812 for controlling opening/closing of first tube 17A. This clamp mechanism 812 has a fixed valve element 821*a* and a movable valve element 812*b* arranged on the outer side of first tube 17A to face each other to sandwich first tube 17A. Stopcock flow path switching device 800A has a switching-linked mechanism 815 for linking the opening/closing operation of clamp mechanism 812 with the pivoting operation of flow path switching cock 810*d*.

(Switching-linked Mechanism 815)

Figure 9:
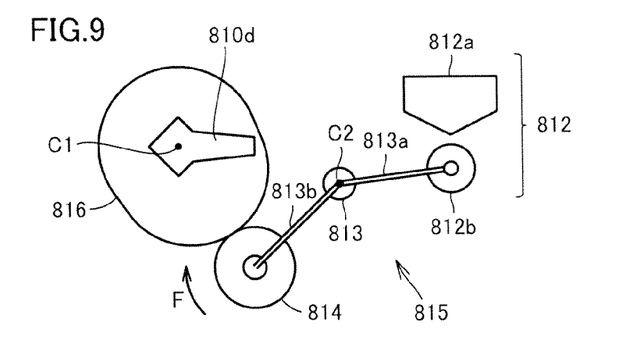
FIG. 9 is a schematic view showing a device configuration when a blood pressure measuring flow path is selected in a switching-linked mechanism used in the stopcock flow path switching device in accordance with the first embodiment.
Figure 10:
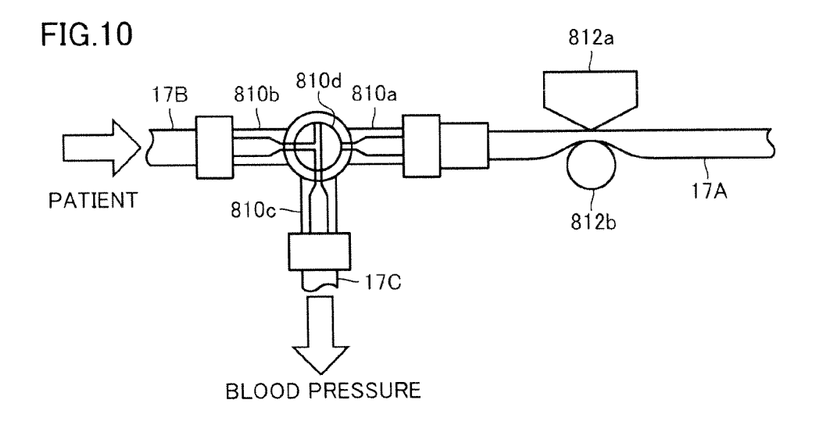
FIG. 10 is a view showing a state in which the blood pressure measuring flow path has been selected in the switching-linked mechanism used in the stopcock flow path switching device in accordance with the first embodiment.
Figure 11:
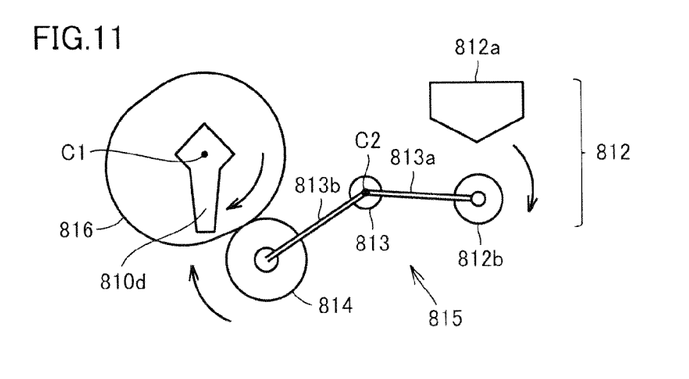
FIG. 11 is a schematic view showing a device configuration when the contrast agent introducing flow path is selected in the switching-linked mechanism used in the stopcock flow path switching device in accordance with the first embodiment.
Figure 12:
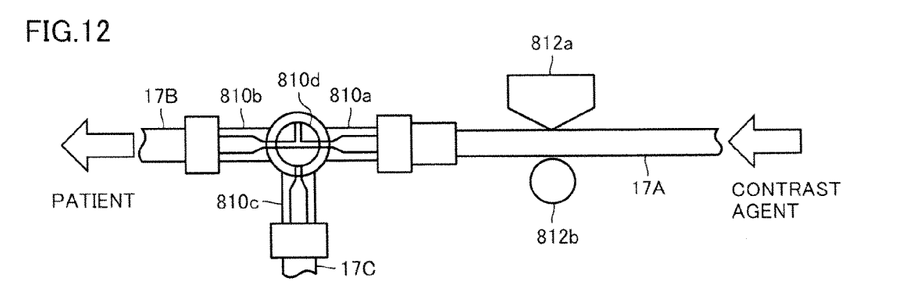
FIG. 12 is a view showing a state in which the contrast agent introducing flow path has been selected in the switching-linked mechanism used in the stopcock flow path switching device in accordance with the first embodiment.

Switching-linked mechanism 815 in accordance with the present embodiment will be described with reference to FIGS. 9 to 12. FIG. 9 is a schematic view showing a device configuration when the blood pressure measuring flow path is selected in switching-linked mechanism 815, and FIG. 10 is a view showing a state in which the blood pressure measuring flow path has been selected in switching-linked mechanism 815. FIG. 11 is a schematic view showing a device configuration when the contrast agent introducing flow path is selected in switching-linked mechanism 815, and FIG. 12 is a view showing a state in which the contrast agent introducing flow path has been selected in switching-linked mechanism 815.

First, a detailed structure of switching-linked mechanism 815 will be described with reference to FIG. 9. Switching-linked mechanism 815 has a supporting part 813 having a rotation center C2. This supporting part 813 is provided with a first link bar 813*a* and a second link bar 813*b* extending from supporting part 813 in different directions.

Movable valve element 812*b* is attached to the tip end of first link bar 813*a*. Movable valve element 812*b* has a cylindrical shape and is fixed to first link bar 813*a* to be rotatable about an axial core thereof. In the present embodiment, an angle at which first link bar 813*a* and second link bar 813*b* intersect is on the order of about 135 degrees. This intersection angle can be changed as appropriate, depending on the device configuration.

A sliding roller 814 is attached to the tip end of second link bar 813b. Sliding roller 814 has a cylindrical shape and is fixed to second link bar 813b to be rotatable about an axial core thereof.

Biasing force F is applied to sliding roller 814 such that sliding roller 814 constantly abuts a side surface of an eccentric cam roller 816. For example, by providing biasing means such as a spring inside supporting part 813, biasing force F can be applied to sliding roller 814 such that sliding roller 814 abuts the side surface of eccentric cam roller 816.

Flow path switching cock 810d of three-way stopcock 810 is provided with eccentric cam roller 816 having a rotation center C1 identical to that of flow path switching cock 810d. Rotation angles of flow path switching cock 810d and eccentric cam roller 816 are controlled by a drive device such as a servo motor, and rotation positions thereof are controlled in a similar manner.

In the state shown in FIG. 9, sliding roller 814 is located at a position farthest from rotation center C1 of eccentric cam roller 816. As shown in FIG. 10, in this rotation position of eccentric cam roller 816, flow path switching cock 810d of three-way stopcock 810 couples a second port 810b to a third port 810c. In addition, movable valve element 812b is located at a position closest to fixed valve element 812a and closes first tube 17A.

Consequently, second tube 17B coupled to second port 810b communicates with third tube 17C coupled to third port 810c, and first tube 17A is closed by clamp mechanism 812 including fixed valve element 821a and movable valve element 812b. This results in the state in which the blood pressure measuring flow path for coupling the patient to blood pressure transducer 300 is formed. In the state in which the blood pressure measuring flow path is formed, stopcock 820 provided in third tube 17C causes third tube 17C to be in the closed state.

One-way valve for allowing a flow of normal saline from the roller pump 400 side to the patient side when roller pump 400 is driven may be provided instead of stopcock 820.

Next, a case of rotating flow path switching cock 810d of three-way stopcock 810 in a clockwise direction by 90 degrees will be described with reference to FIGS. 11 and 12. In the state shown in FIG. 11, sliding roller 814 is located at a position closest to rotation center C1 of eccentric cam roller 816.

As shown in FIG. 12, in this rotation position of eccentric cam roller 816, flow path switching cock 810d of three-way stopcock 810 couples a first port 810a to second port 810b. In addition, movable valve element 812b of clamp mechanism 812 is located at a position farthest from fixed valve element 812a and opens first tube 17A.

Consequently, first tube 17A coupled to first port 810a communicates with second tube 17B coupled to second port 810b, and third tube 17C is closed. This results in the state in which the flow path contrast agent introducing flow path for coupling the patient to the injector head is formed.

In the case of shifting from the state in which the flow path contrast agent introducing flow path is formed (the state shown in FIGS. 11 and 12) to the state in which the blood pressure measuring flow path is formed (the state shown in FIGS. 9 and 10), flow path switching cock 810d is rotated in a counterclockwise direction by 90 degrees.

As described above, in stopcock flow path switching device 800A in accordance with the present embodiment, three-way stopcock 810 is used to switch between the state in which the flow path contrast agent introducing flow path for coupling the patient to the injector head is formed by communicating first tube 17A with second tube 17B and closing third tube 17C, and the state in which the blood pressure measuring flow path for coupling the patient to the transducer is formed by communicating first tube 17A with third tube 17C and closing second tube 17B. Consequently, the blood pressure of the patient is applied to the blood pressure transducer via three-way stopcock 810, and thus, the blood pressure of the patient can be measured more accurately.

In addition, in stopcock flow path switching device 800A, switching-linked mechanism 815 is used. Therefore, in the state in which the blood pressure measuring flow path for coupling the patient to the transducer is formed, first tube 17A coupled to the injector head side is closed by clamp mechanism 812 due to the link mechanism. Consequently, it is also possible to prevent an infective substance from entering the injector head side when the blood pressure of the patient is measured.

In the present embodiment, the case of using the link mechanism shown in FIG. 9 as switching-linked mechanism 815 has been described. However, without using the link mechanism, a control device can also be used to separately execute rotation angle control for flow path switching cock 810d and position control for movable valve element 812b of clamp mechanism 812.

In addition, clamp mechanism 812 has such a configuration that first tube 17A is clamped by fixed valve element 812a and movable valve element 812b. However, both valve elements can also be movable valve elements.

(Second Embodiment)

Figure 13:
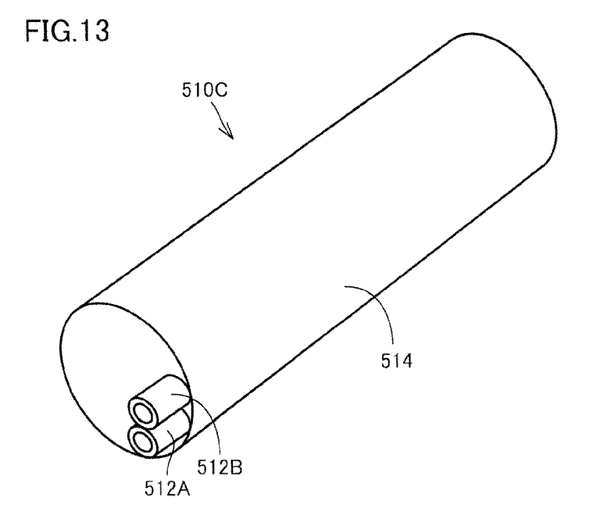
FIG. 13 is an overall perspective view showing a configuration of a syringe in accordance with a second embodiment.
Figure 15:
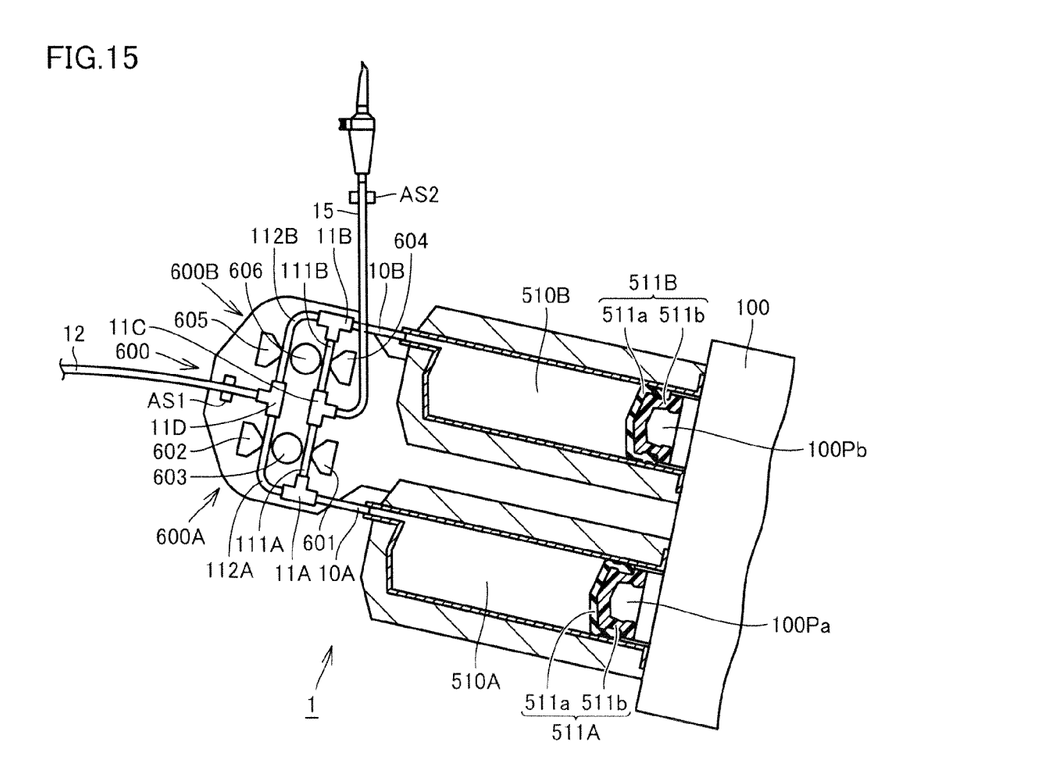
FIG. 15 is a view showing a flow path configuration and a configuration of a liquid medicine flow path switching device in accordance with the related art.
Figure 16:
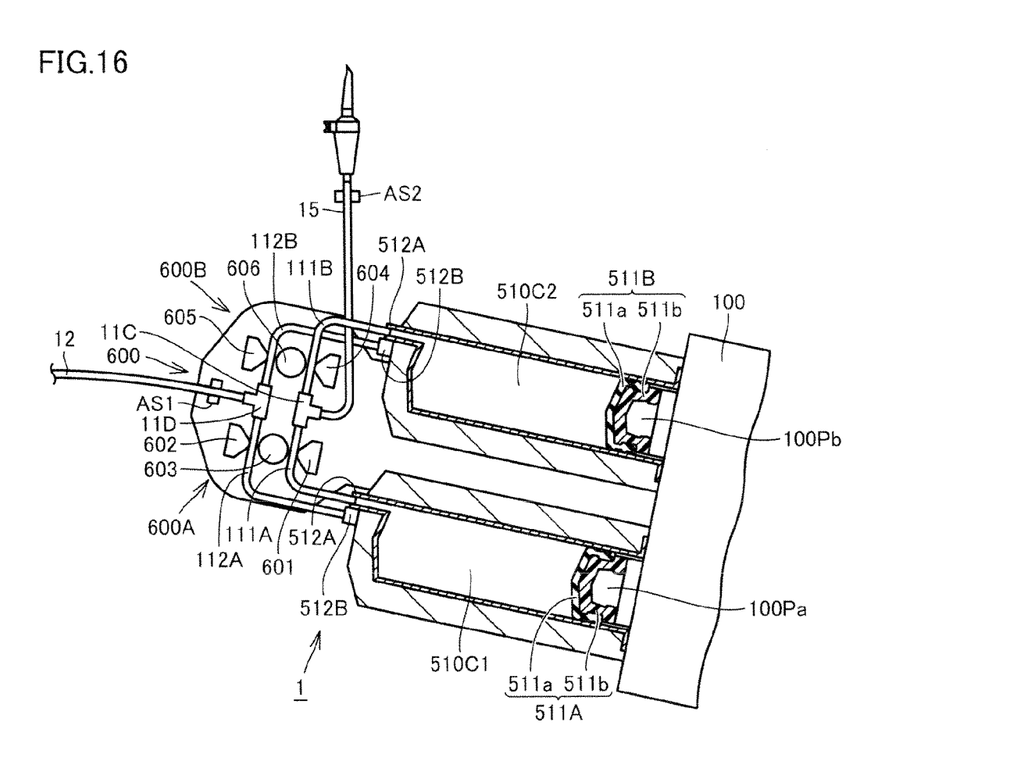
FIG. 16 is a view showing a flow path configuration and a configuration of a liquid medicine flow path switching device when the syringe in accordance with the second embodiment is used.

Next, a syringe 510C attached to the injector head in accordance with the present embodiment will be described with reference to FIGS. 13 to 16. FIG. 13 is an overall perspective view showing a configuration of the syringe in accordance with the present embodiment, FIG. 14 is a side view showing the configuration of the syringe in accordance with the present embodiment, FIG. 15 is a view showing a flow path configuration and a configuration of a contrast agent flow path switching device in accordance with the related art, and FIG. 16 is a view showing a flow path configuration and a configuration of a contrast agent flow path switching device when the syringe in accordance with the present embodiment is used.

Figure 14:
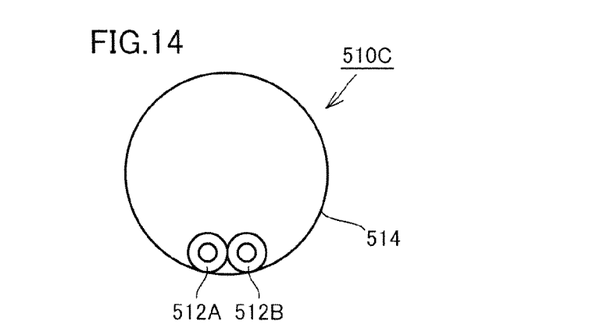
FIG. 14 is a side view showing the configuration of the syringe in accordance with the second embodiment.

Referring to FIGS. 13 and 14, the basic configuration of syringe 510C in accordance with the present embodiment is the same as those of syringes 510A and 510B described with reference to FIGS. 5 and 6, and a difference is that two through holes 512A and 512B are provided side by side on the same side on the tip end side of cylindrical part 514.

The flow path configuration and the configuration of liquid medicine flow path switching device 600 in accordance with the related art will now be described with reference to FIG. 15. Liquid medicine flow path switching device 600 should be indicated by a broken line because the main components are located on the opposite side of the device. However, for the sake of convenience in description, liquid medicine flow path switching device 600 is indicated by a solid line in FIG. 15.

First, the flow path configuration will be described. To injector head body 100, first syringe 510A having contrast agent Z filled therein and second syringe 510B having contrast agent Z filled therein are mounted. A first piston 511A coupled to a first plunger 100Pa is provided inside first syringe 510A, and a second piston 511B coupled to a second plunger 100Pb is provided inside second syringe 510B.

One end of a first tube 10A is coupled to first syringe 510A. The other end of first tube 10A is coupled to a first T-shaped tube 11A. To first T-shaped tube 11A, one end of a third tube 111A and one end of a fifth tube 112A are coupled, respectively.

One end of a second tube 10B is coupled to second syringe 510B. The other end of second tube 10B is coupled to a second T-shaped tube 11B. To second T-shaped tube 11B, one end of a fourth tube 111B and one end of a sixth tube 112B are coupled, respectively.

Third and fourth tubes 111A and 111B each have the other end coupled to a third T-shaped tube 11C. To third T-shaped tube 11C, seventh tube 15, having the other end coupled to contrast agent bag 16, is coupled.

Fifth and sixth tubes 112A and 112B each have the other end coupled to a fourth T-shaped tube 11D. To fourth T-shaped tube 11D, coupling tube 12, having the other end coupled to connector 13, is coupled.

A first air sensor AS1 detecting entrance of air to the tube is provided on coupling tube 12, and a second air sensor AS2 detecting entrance of air to the tube is provided on seventh tube 15.

(Liquid Medicine Flow Path Switching Device 600)

Liquid medicine flow path switching device 600 is provided for switching opening/closing of third tube 111A and opening/closing of fifth tube 112A. This liquid medicine flow path switching device 600 has a first flow path switching mechanism 600A and a contrast agent/blood pressure flow path switching mechanism 600B.

First flow path switching mechanism 600A is provided for switching between third and fifth tubes 111A and 112A arranged parallel to each other, and contrast agent/blood pressure flow path switching mechanism 600B is provided for switching between fourth and sixth tubes 111B and 112B arranged parallel to each other.

First flow path switching mechanism 600A has a first change-over valve element 603 provided between third and fifth tubes 111A and 112A and movable in a direction intersecting the direction of extension of the tubes. Further, first flow path switching mechanism 600A has first and second fixed valve elements 601 and 602 at positions opposite to first change-over valve element 603 with respective tubes interposed.

Similarly, contrast agent/blood pressure flow path switching mechanism 600B has a second change-over valve element 606 provided between fourth and sixth tubes 111B and 112B and movable in a direction intersecting the direction of extension of the tubes. Further, contrast agent/blood pressure flow path switching mechanism 600B has third and fourth fixed valve elements 604 and 605 at positions opposite to second change-over valve element 606 with respective tubes interposed.

Next, the flow path configuration in the case of using a syringe 510C1 and a syringe 510C2 in accordance with the present embodiment as shown in FIGS. 13 and 14 will be described with reference to FIG. 16. The configuration of liquid medicine flow path switching device 600 is the same as that in the related art.

The flow path configuration in the case of using syringe 510C1 in accordance with the present embodiment is such that one end of third tube 111A is coupled to through hole 512A of syringe 510C1 and one end of fifth tube 112A is coupled to through hole 512B of syringe 510C1. Consequently, the use of first T-shaped tube 11A is unnecessary, as compared with the flow path configuration shown in FIG. 15.

Similarly, the flow path configuration in the case of using syringe 510C2 in accordance with the present embodiment is such that one end of fourth tube 111B is coupled to through hole 512A of syringe 510C2 and one end of sixth tube 112B is coupled to through hole 512B of syringe 510C2. Consequently, the use of second T-shaped tube 11B is unnecessary, as compared with the flow path configuration shown in FIG. 15.

As described above, when syringe 510C1 or 510C2 having two through holes 512A and 512B in accordance with the present embodiment is used, the number of the used T-shaped tubes for branching the flow path can be reduced.

While the embodiments of the present invention have been described above, it should be understood that the embodiments disclosed herein are illustrative and not limitative in any respect. The scope of the present invention is defined by the terms of the claims, and is intended to include any modifications within the scope and meaning equivalent to the terms of the claims.

REFERENCE SIGNS LIST 1 injector head; 10A first tube; 10B second tube; 11A first T-shaped tube; 11B second T-shaped tube; 11C third T-shaped tube; 11D fourth T-shaped tube; 12 coupling tube; 13, 14, 20, 21, 25, 26 connector; 15 seventh tube; 16 contrast agent bag; 17 main tube; 17A first tube (first flow path); 17B second tube (second flow path); 17C third tube (third flow path); 17a branch tube; 17t T-shaped tube; 19 normal saline tube; 22 tube; 27 saline bag; 100 injector head body; 100Pa first plunger; 100Pb second plunger; 100a first surface; 100b second surface; 100c third surface; 100d fourth surface; 110 operation monitor; 111A third tube; 111B fourth tube; 112A fifth tube; 112B sixth tube; 300 blood pressure transducer; 400 roller pump; 510A, 510B, 510C, 510C1, 510C2 syringe; 511 piston; 511A first piston; 511B second piston; 511a piston rubber; 511b piston core; 512, 512A, 512B through hole; 513 flange; 514 cylindrical part; 600 liquid medicine flow path switching device; 600A first flow path switching mechanism; 600B contrast agent/blood pressure flow path switching mechanism; 601 first fixed valve element; 602 second fixed valve element; 603 first change-over valve element; 604 third fixed valve element; 605 fourth fixed valve element; 606 second change-over valve element; 700 rotating part; 800 contrast agent/blood pressure flow path switching device; 800A stopcock flow path switching device; 801 change-over valve element; 802, 803 fixed valve element; 810 three-way stopcock; 810a first port; 810b second port; 810c third port; 810d flow path switching cock; 812 clamp mechanism; 812b movable valve element; 813 supporting part; 813a first link bar; 813b second link bar; 814 sliding roller; 815 switching-linked mechanism; 816 eccentric cam roller; 820 stopcock; 821a fixed valve element; 900 support post; 1000L contrast agent introducing flow path; AL rotation axis; AS1 first air sensor; AS2 second air sensor; AS3 third air sensor; C1 rotation center; C2 rotation center; P 100; S1 multi-use section; S2, S3 one-time use section; SL central axis line.

The invention claimed is:

1. A stopcock flow path switching device used to switch between a contrast agent introducing flow path for introducing a contrast agent into a patient by using an injector head and a blood pressure measuring flow path for measuring a blood pressure of said patient by using a blood pressure transducer, the stopcock flow path switching device comprising:
   a three-way stopcock having a flow path switching cock and provided to, by switching of said flow path switching cock, allow flow path switching between a state in which said contrast agent introducing flow path is formed by coupling a flow path on said patient side to a flow path on said injector head side and a state in which said blood pressure measuring flow path is formed by coupling the flow path on said patient side to a flow path on said blood pressure transducer side;

a clamp mechanism for closing the flow path of said three-way stopcock communicating with said injector head side, in the state in which said blood pressure measuring flow path is formed; and a switching-linked mechanism for controlling said clamp mechanism in accordance with a switching position of said flow path switching cock of said three-way stopcock, such that a first flow path coupled to said three-way stopcock and communicating with said injector head side is opened in the state in which said contrast agent introducing flow path is formed, and said first flow path coupled to said three-way stopcock and communicating with said injector head side is blocked in the state in which said blood pressure measuring flow path is formed, wherein said clamp mechanism has a fixed valve element and a movable valve element arranged on an outer side of said first flow path to face each other to sandwich said first flow path, and said switching-linked mechanism moves said movable valve element to a position farthest from said fixed valve element and opens said first flow path in the state in which said contrast agent introducing flow path is formed, and moves said movable valve element to a position closest to said fixed valve element, sandwich said first flow path between said movable valve element and said fixed valve element and blocks said first flow path in the state in which said blood pressure measuring flow path is formed, said switching-linked mechanism includes:
an eccentric cam roller provided at said flow path switching cock and provided to have a rotation center identical to that of said flow path switching cock;
a supporting part having a rotation center;
a first link bar and a second link bar provided at said supporting part and extending from said supporting part in different directions;
said movable valve element provided at a tip end of said first link bar; and
a sliding roller provided at a tip end of said second link bar and constantly abutting a side surface of said eccentric cam roller, in the state in which said contrast agent introducing flow path is formed, said sliding roller is located at a position closest to said rotation center of said eccentric cam roller and said movable valve element is located at the position farthest from said fixed valve element, and in the state in which said blood pressure measuring flow path is formed, said sliding roller is located at a position farthest from said rotation center of said eccentric cam roller and said movable valve element is located at the position closest to said fixed valve element.

2. The stopcock flow path switching device according to claim 1, wherein in the flow path on said blood pressure transducer side, a stopcock is provided for opening and closing said flow path on an opposite side of said three-way stopcock with said blood pressure transducer interposed therebetween.

* * * * *